US008653259B2

(12) United States Patent
Heinelt et al.

(10) Patent No.: US 8,653,259 B2
(45) Date of Patent: Feb. 18, 2014

(54) PROCESS FOR SYNTHESIZING HETEROCYCLIC COMPOUNDS

(75) Inventors: Uwe Heinelt, Weisbaden (DE); Hans-Jochen Lang, Hofheim (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 384 days.

(21) Appl. No.: 12/026,746

(22) Filed: Feb. 6, 2008

(65) Prior Publication Data

US 2008/0146797 A1    Jun. 19, 2008

Related U.S. Application Data

(63) Continuation of application No. 10/840,105, filed on May 6, 2004, now abandoned.

(60) Provisional application No. 60/507,143, filed on Sep. 30, 2003.

(30) Foreign Application Priority Data

May 22, 2003  (DE) .................................. 103 23 701

(51) Int. Cl.
| | |
|---|---|
| C07D 233/50 | (2006.01) |
| C07D 235/20 | (2006.01) |
| C07D 235/04 | (2006.01) |
| C07D 235/02 | (2006.01) |
| C07D 263/28 | (2006.01) |
| C07D 263/58 | (2006.01) |
| C07D 263/52 | (2006.01) |
| C07D 265/08 | (2006.01) |
| C07D 265/06 | (2006.01) |
| C07D 265/12 | (2006.01) |
| C07D 265/18 | (2006.01) |
| C07D 277/18 | (2006.01) |
| C07D 277/08 | (2006.01) |
| C07D 409/12 | (2006.01) |
| C07D 409/02 | (2006.01) |
| C07D 413/12 | (2006.01) |
| C07D 495/04 | (2006.01) |
| C07D 233/06 | (2006.01) |

(52) U.S. Cl.
USPC ............ 544/88; 544/90; 546/271.1; 548/190; 548/222; 548/303.7; 548/304.7; 548/307.4; 548/333.1

(58) Field of Classification Search
None
See application file for complete search history.

(56) References Cited

U.S. PATENT DOCUMENTS 3,847,934 A * 11/1974 Neumann ................... 548/311.7
7,049,333 B2 * 5/2006 Lang et al. .................... 514/388

FOREIGN PATENT DOCUMENTS

WO  WO 03/052434   6/2003
WO  WO 03/101984  12/2003

OTHER PUBLICATIONS

Isothiocyanates, http://www.sigmaaldrich.com/catalog/Lookup.do?N5=All&N3=mode+matchpartialmax&N4=isothiocyanate&D7=0&D10=isothiocyanate&N1=S_ID&ST=RS&N25=0&F=PR (2010).*
Abstract, Reactiones Organicae: New methods in synthetic organic chemistry selected from the current chemical literature., Synthesis, 1974, pp. 41-42.
Fell, JB., et al., A Mild and Efficient Preparation of Carbodimides, Synthetic Communications, vol. 25(1), 1995, pp. 43-47.
Ferenc, F., et. al., Synthesis of Steroisomeric Condensed-Skeleton 2-imino-substituted 1,3-oxazines, Tetrahedron, vol. 41, No. 24, 1985, pp. 5981-5988.

(Continued)

*Primary Examiner* — Sun Jae Loewe
(74) *Attorney, Agent, or Firm* — Scully, Scott, Murphy & Presser, P.C.

(57) ABSTRACT

The invention provides the process illustrated in scheme 1 for synthesizing heterocyclic compounds of formula I.

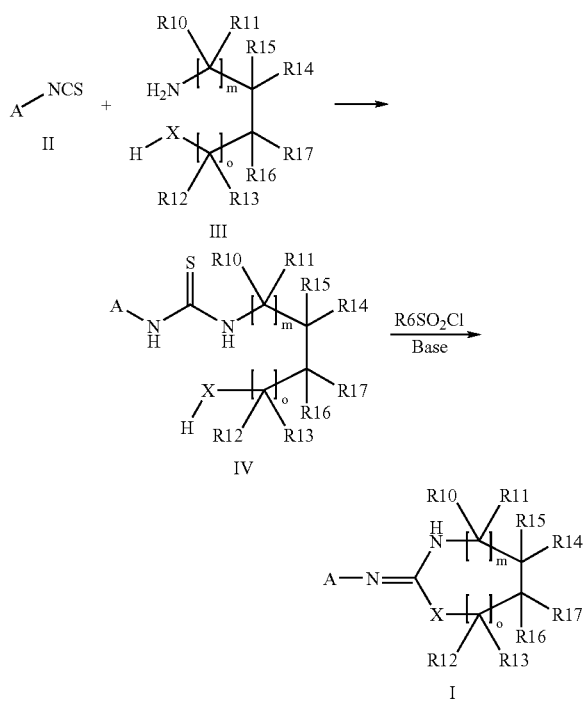

In the process, an isothiocyanate of formula II is initially reacted with a primary amine or formula III to give a thiourea of formula IV. Subsequently, the thiourea of formula IV is converted to the corresponding heterocycle of formula I using a base and a sulfonyl chloride.

11 Claims, No Drawings

(56) References Cited

OTHER PUBLICATIONS

Goerdeler, J., et. al., Substituierte Thiazolin-dione-(4,5) und ihre thermische Spaltung in Isocyanate und Senfole, Chemische Berichte. vol. 99, No. 11, 1966, pp. 3572-3581.

Isobe, T., et. al., Preparation of 1,3-Unsubstituted and 1-Substituted 2-Iminoimidazolidine Derivatives and a Related Guanidine by the 2-Chloro-1,3-dimethylimidazolinium Chloride-Induced Cyclization of Thioureas, J. Org. Chem., vol. 65, 2000, pp. 7774-7778.

Jen, T., et. al., Amidines and Related Comounds. 6. 1 Studies on Structure-Activity Relationships of Antihypertensive and Antisecretory Agents Related to Clonidine, Journal of Medicinal Chemistry, vol. 18, No. 1, 1975, pp. 90-99.

Kim, Th. et. al., A mild cyclodesulfurization of N-(2-hydroxyethyl)-N1-phenylthioureas to 2-phenylamino-2-oxazolines using TsCl/NaOH, Tetrahedron, vol. 57, 2001, pp. 7137-7141.

Kim, Th, et. al, One-pot synthesis of 2-phenylaminothiazolines from N-(2-hydroxyethyl)-N1-phenylthioureas, Tetrahedron Letters, vol. 40, 1999, pp. 8201-8204.

Kim, Th, et al., One-pot synthesis of 2-phenylaminothiazolines from N-(2-hydroxyethyl)-N'-phenylthioureas, Tetrahedron Letters, vol. 42, 2001; pp. 2413.

Kim, Th, et. al., N-Acyl-4,5-dihydro-4,4-dimethyl-N-methyl-2-thiazolamine as a chemoselective acylating agent, Tetrahedron Letters, vol. 43, 2002, pp. 9553-9557.

Krchnak, V. et al., A solid phas traceless synthesis of 2-arylaminobenzimidazoles, Tetrahedron Letters, Bol. 42, 2001, pp. 1627-1630.

Lee, G-J., et al., Investigation of the Cyclization of N-(2-Hydroxyethyl)-N1-phenylthioureas: Mitsunobu Conditons vs TsCl/NaOH System, Bull. Korean Chem. Soc., vol. 23, No. 1, 2002, pp. 19-20.

Matsuo, M., et. al., New 2-Aryliminoimidazolidines. I. Synthesis and Antihypertensive Properties of 2-(2-Phenoxyphenylimino)imidazolidines and Related Compounds, Chemical and Pharmaceutical Bullentin, Pharmaceutical Society of Japan, vol. 33, No. 10, Oct. 1985, pp. 4409-4421.

Mohsen, A., et al., The Cyclodesulfurization of Thio-compounds, Pharmazie, vol. 35, 503, 1980, pp. 798-799.

Mohsen, A., et, al., The Cyclodesulfurization of Thio Compounds; XVI. Dicyclohexylcarbodiimide a an Efficient Cyclodesulfurizing Agent in the Synthesis of Heterocyclic Compounds from Various Thio Compounds, Synthesis, 1977, pp. 864-865.

Seth, P. P., et. al., Efficient solution phase synthesis of 2-(N-acyl)-aminobenzimidazoles, Tetrahedron Letters, vol. 43, No. 41, Oct. 2002, pp. 7303-7306.

Williams, A., et. al., Carbodiimide Chemistry: Recent Advances, Chem. Rev. (1981) Voll. 81, pp. 599-636.

\* cited by examiner

PROCESS FOR SYNTHESIZING HETEROCYCLIC COMPOUNDS

CROSS-REFERENCE TO RELATED APPLICATIONS

This application is a continuation of U.S. application Ser. No. 10/840,105, filed May 6, 2004 which claims the benefit of priority of German Patent Application No. 10323701.1, filed May 22, 2003, as well as the benefit of U.S. Provisional Patent Application No. 60/507,143, filed Sep. 30, 2003.

FIELD OF THE INVENTION

The invention provides the process illustrated in scheme 1 for synthesizing the heterocyclic compounds of formula I.

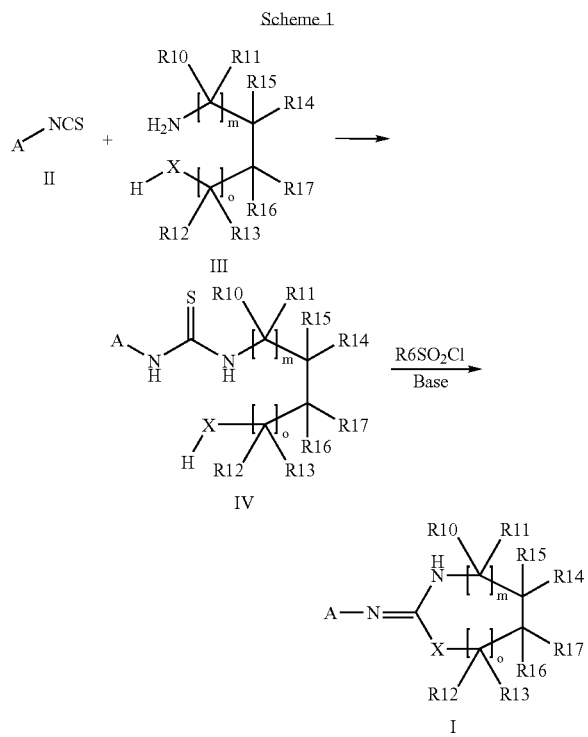

In the process of the invention, an isothiocyanate of formula II is initially reacted with a primary amine of formula III to give a thiourea of formula IV. Subsequently, the thiourea of the formula IV is converted to the corresponding heterocycle of formula I, using a base and a sulfonyl chloride.

BACKGROUND OF THE INVENTION

The construction of basic heterocyclic structures is one of the most important synthetic steps in organic chemistry. The heterocyclic compounds are of great significance, inter alia, as intermediates in the synthesis of active pharmaceutical ingredients and active crop protection ingredients, or else directly as such active ingredients. In addition, the rapid synthesis, which is particularly important in the preparation of screening substances, analogs of which are sometimes quite diverse in structural terms, places high demands on synthesis planning. Central building blocks which allow direct access to a multitude of diverse heterocycles under similar, or ideally identical, reaction conditions are therefore particularly valuable and of great significance, in particular for robot-assisted syntheses.

The synthesis of heterocycles starting from thioureas has been known for some time. However, the methods have limitations in substrate selection or disadvantages in reaction control, workup, by-product removal or in the cost of reagents. For instance, 1-(2-hydroxyethyl)-3-arylthioureas can be cyclyzed by heavy metal derivatives, such as mercury (II) oxide or lead oxide, to give oxazolidin-2-ylidenarylamines (Jen, et al., J. Med. Chem. 1975 (18), 90). Acid catalysis of the same reactants affords the corresponding arylthiazolidin-2-ylidenamines (Jen, et al., J. Med. Chem. 1975 (18), 90). However, the use of heavy metals is disadvantageous, since they are unwanted in the product, even only in trace amounts. The acid-catalyzed conversion to the thiazolidine again proceeds satisfactorily only at elevated temperatures and in the presence of high acid concentrations. These drastic conditions are not tolerated by some functionalities, such as esters, nitrites and ketals.

Syntheses starting from 1-(2-aminoethyl)-3-arylthioureas to imidazolidin-2-ylidenaryl derivatives succeed in the presence of methyl iodide (Synthesis 1974, 41-42) or carbodiimide derivatives (Synthesis 1977, 864). A disadvantage in the case of methyl iodide is the competing reaction which occurs on other nucleophilic centers in the molecule and the consequent potential danger in the event of unintentional release. In the case of carbodiimide derivatives, the removal of the ureas formed is frequently problematic and time-consuming. More recent carbodiimide derivatives such as EDC (N'-(3-dimethylaminopropyl)-N-ethylcarbodiimide hydrochloride) or solid phase-bound DCC (dicyclohexylcarbodiimide), used in a relatively large amount, are again very expensive.

SUMMARY OF THE INVENTION

The synthetic method of the present invention, starting from isothiocyanates and amino alcohols, amino mercaptans and diamines, via the thioureas formed as intermediates, leads to the desired heterocycles of variable ring size, by cyclizing the intermediate derivatives in the presence of sulfonyl chloride and of a base. These reagents are inexpensive, easy to handle and require no drastic reaction conditions, and their resulting products are easy to remove by simple washings, so that this synthetic process is suitable, for example, for reactions on the gram and kilogram scale. However, it can also be employed for parallel and robot syntheses which are usually carried out on the milligram scale, especially owing to the simple reaction control. Of particular interest for these synthetic methods, which are generally employed on a relatively small scale, is the use of polymer-bound sulfonyl chloride, which enables the isolation of the reaction products by filtration and evaporation steps which are simple from an apparatus point of view.

In the literature, a similar process method is found, quite specifically for the reaction of phenyl or methyl isothiocyanates with 2-hydroxyethylamines to give oxazolidin- or thiazolidin-2-ylidenamines (Tetrahedron Letters 40 (1999), 8201; Tetrahedron 57 (2001), 7137; Bull. Korean Chem. Soc. 2002 (23), 19).

It has now been found, surprisingly, that, under these conditions, not only can five-membered rings such as oxazolidines or thiazolidines be formed, but also that ring size and degree of substitution are much more flexible and the synthetic method is not restricted to the use of 2-hydroxyethylamines. Restriction to thiourea intermediates which bear at least one aryl substituent on one of the thiourea nitrogens results in the ring closure proceeding very selectively and affording, with the loss of the thiourea sulfur, generally only one cyclization product.

The present invention thus relates to a process for preparing heterocycles of formula I

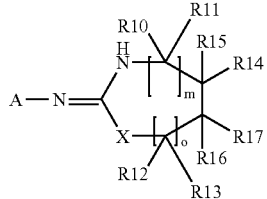

wherein:
X is sulfur, oxygen or NR5
  wherein R5 is hydrogen or (C1-C4)alkyl;
m and o are each independently zero, 1 or 2;
A is either a) phenyl, naphthyl or heteroaryl, each of which is optionally substituted by 1, 2, 3, 4 or 5 R11 radicals
  wherein R11 is, in each case, independently selected from the group consisting of (C1-C4)alkyl, F, Cl, Br, I, CN, NO$_2$, OH, O(C1-C4)alkyl, and COO(C1-C4)alkyl, and some or all of the hydrogen atoms of the alkyl radicals may be replaced by fluorine atoms;
  or b) selected from (C1-C4)alkyl, (C2-C5)alkenyl, (C2-C5)alkynyl, (C3-C8)cycloalkyl, and (C4-C8)cycloalkenyl radicals
  wherein said radicals may each independently be substituted by (C1-C4)alkyl or (C3-C6)cycloalkyl, and
  wherein some or all of the hydrogen atoms of the alkyl, alkenyl, alkynyl, cycloalkyl and cycloalkenyl radicals may be replaced by fluorine atoms;
R14, R15, R16 and R17
  are each independently selected from hydrogen, F and (C1-C4)alkyl, wherein some or all of the hydrogen atoms of the alkyl radicals may be replaced by fluorine atoms;
or
R14 and R16 together are a bond, and
R15 and R17, together with the two carbon atoms to which they are bonded, form an aromatic six-membered carbocycle, in which one or two carbon atoms may be replaced by nitrogen, or a thiophene ring,
  wherein the aromatic six-membered carbocycle and the thiophene ring is optionally substituted by 1, 2, 3 or 4 R7 radicals,
  wherein R7 is, in each case, independently selected from the group consisting of (C1-C4)alkyl, F, Cl, Br, I, CN, NO$_2$, OH, O(C1-C4)-alkyl and COO(C1-C4)alkyl, and some or all of the hydrogen atoms of the alkyl radicals may be replaced by fluorine atoms;
or
R14 and R16 are each independently hydrogen or (C1-C4)alkyl,
  wherein some or all of the hydrogen atoms of the alkyl radicals may be replaced by fluorine atoms;
and
R15 and R17, together with the two carbon atoms to which they are bonded, form a saturated 5-, 6-, 7- or 8-membered carbocycle in which one or two carbon atoms may each independently be replaced by O, S, NH or N(C1-C4)alkyl and may be substituted by 1, 2, 3, 4, 5 or 6 R8 radicals
  wherein R8 is, in each case, independently selected from the group consisting of (C1-C4)alkyl, O(C1-C4)alkyl, and COO(C1-C4)alkyl, and some or all of the hydrogen atoms of the alkyl radicals may be replaced by fluorine atoms;
R10, R11, R12 and R13
  are each independently hydrogen, F or (C1-C4)alkyl,
    wherein some or all of the hydrogen atoms of the alkyl radicals may be replaced by fluorine atoms;
wherein, either (i) A is an aromatic ring system, or (ii) the ring formed from R15 and R17 is an aromatic system and m is zero, or (iii) each of A and the ring formed from R15 and R17 is an aromatic ring system; and their tautomers and their salts;
provided, however, that compounds in which A is unsubstituted phenyl or (C1-C4)alkyl; and X is oxygen; and R14 and R15 are each independently hydrogen, (C1-C4)alkyl or benzyl; and R16 and R17 are each hydrogen; and m and o are each zero are excluded;
which process comprises, as shown in scheme 1,

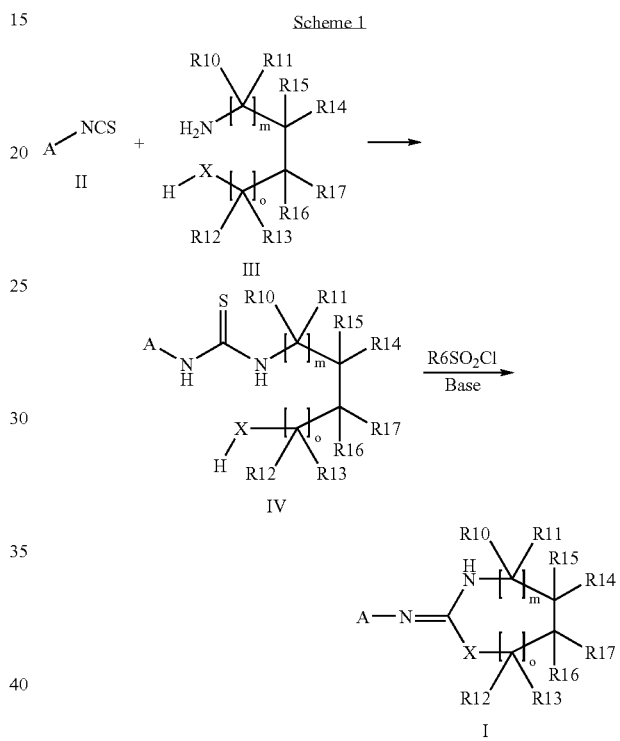

a) reacting an isothiocyanate of formula II with a primary amine of formula III to give a thiourea of formula IV, and
b) converting the thiourea of formula IV, using a sulfonyl chloride R6SO$_2$Cl in the presence of a base, to said compound of formula I,
where, in the compounds of the formulae II, III and IV, A, X, n, m and R10 to R17 are each as defined in formula I and R6 is (C1-C4)alkyl, trifluoromethyl or phenyl which is unsubstituted or substituted by methyl, trifluoromethyl, F, Cl, Br or a polymeric support.

DETAILED DESCRIPTION OF THE INVENTION

A further embodiment of the present invention relates to a process for preparing heterocycles of formula Ia, Ia wherein:
X is sulfur, oxygen or NR5,
  where R5 is hydrogen or (C1-C4)alkyl;

n is zero, 1, 2 or 3;

Ar is phenyl, naphthyl or heteroaryl, each of which may be optionally substituted by 1, 2, 3, 4 or 5 R11 radicals where R11 is in each case independently selected from the group consisting of (C1-C4)alkyl, F, Cl, Br, I, CN, $NO_2$, OH, O(C1-C4)-alkyl, and COO(C1-C4)alkyl, and some or all of the hydrogen atoms of the alkyl radicals may be replaced by fluorine atoms;

R1, R2, R3 and R4 are each independently hydrogen, F or (C1-C4)alkyl where some or all of the hydrogen atoms of the alkyl radicals may be replaced by fluorine atoms;

or

R1 and R3 together are a bond, and

R2 and R4, together with the two carbon atoms to which they are attached, form an aromatic six-membered carbocycle in which one or two carbon atoms may be replaced by nitrogen and the aromatic six-membered ring may be substituted by 1, 2, 3 or 4 R7 radicals, where R7 is in each case independently selected from the group consisting of (C1-C4)alkyl, F, Cl, Br, I, CN, $NO_2$, OH, O(C1-C4)-alkyl, and COO(C1-C4)alkyl, and some or all of the hydrogen atoms of the allyl radicals may be replaced by fluorine atoms, where n=0;

or

R1 and R3 are each independently hydrogen or (C1-C4)alkyl and

R2 and R4, together with the two carbon atoms to which they are attached, form a saturated 5-, 6-, 7- or 8-membered carbocycle in which one or two carbon atoms may be replaced by O, S, NH and N(C1-C4)alkyl and which carbocycle may be substituted by 1, 2, 3, 4, 5 or 6 R8 radicals where R8 is in each case independently selected from the group consisting of (C1-C4)alkyl, O(C1-C4)alkyl, and COO(C1-C4)alkyl, and some or all of the hydrogen atoms of the alkyl radicals may be replaced by fluorine atoms, where n=0;

excluding compounds in which Ar is unsubstituted phenyl, X is oxygen or sulfur, R1 and R2 are each independently hydrogen, (C1-C4)alkyl or benzyl, R3 and R4 are each hydrogen and n is zero, and their tautomers and their salts, which process comprises, as shown in scheme 2

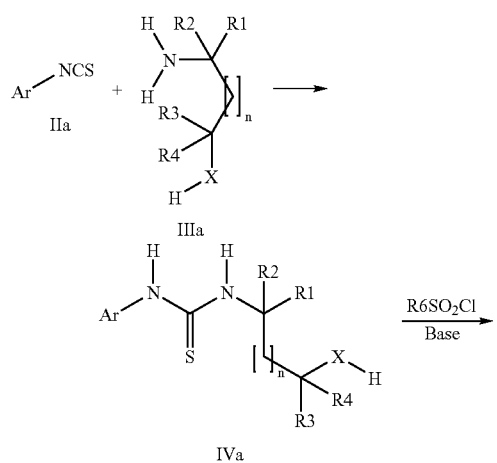

-continued

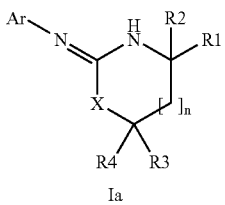

a) reacting an aromatic isothiocyanate of formula IIa with a primary amine of formula IIIa to give a thiourea of formula IVa, and b) converting the thiourea of formula Iva, using a sulfonyl chloride $R6SO_2Cl$ in the presence of a base, to the corresponding compound of formula Ia, where, in the compounds of formulae IIa, IIIa and IVa, Ar, X, n and R1 to R4 are each as defined in formula Ia and R6 is phenyl which is unsubstituted or substituted by methyl, trifluoromethyl, F, Cl or Br.

The compounds of formula Ia are a subset of the compounds of formula I; similarly the compounds of formulae IIa, IIa, and IVa are, respectively, subsets of the compounds of formulae II, III, and IV.

Process step a) may be effected continuously or batchwise. The reaction of the isothiocyanate of formula II with the primary amine of formula III may be carried out in the presence of a solvent or diluent, or without the addition of a solvent.

Preference is given to carrying it out in the presence of a solvent. It is possible to use various solvents, for example aliphatic or aromatic hydrocarbons, chlorinated hydrocarbons, for example methylene chloride, esters, for example ethyl acetate, alcohols or ethers. Preference is given to using ethers as the solvent, for example tetrahydrofuran, dioxane or ethylene glycol ethers such as ethylene glycol dimethyl ether, especially when the overall reaction is carried out as a one-pot reaction. It is also possible to use mixtures of two or more solvents. The temperature for the reaction in process step a) is preferably from 0° C. to the boiling point of the solvent used, more preferably from 20° C. to 60° C., for example about room temperature. The isothiocyanate of formula II and the primary amine of formula III are used, for example, in a molar ratio of from 1:1.1 to 1:0.9, preferably in about equimolar amounts. However, it is also possible to use an excess of the amine of formula III, for example when X is NR5, in order to prevent side reactions.

Process step b) may be effected continuously or batchwise. In general, the conversion of the thiourea of formula IV to the compound of formula I may be carried out in the presence of a solvent or diluent. It is possible to use various solvents, for example esters or ethers, preferably ethers, for example tetrahydrofuran, dioxane or ethylene glycol ethers such as ethylene glycol dimethyl ether. The solvent used may also be water. It is also possible to use mixtures of two or more solvents, for example mixtures of water and one or more organic solvents, for example mixtures of water and one of the ethers mentioned. The reaction may proceed as a monophasic reaction or as a biphasic reaction. The temperature for the reaction in process step b) is preferably from 0° C. to 35° C., more preferably about room temperature. The thiourea of formula IV and the sulfonyl chloride, $R6SO_2Cl$ are used, for example, in a molar ratio of from 1:1.4 to 1:0.9, preferably in a ratio of from 1:1 to 1:1.2, for example in the ratio of about 1:1.1. When polymer-bound sulfonyl chloride is used, the ratio may be from 1:1 to 1:4, preferably from 1:1.5 to 2.5. The molar ratio of the thiourea of formula IV to the base in process step b) is, for example, from 1:4 to 1:1, preferably from 1:3 to 1:2, for example in the ratio of about 1:2.5. The base used in process step b) may be selected from various inorganic or organic compounds, for example basic alkali metal compounds or alkaline earth metal compounds, in particular the metal hydroxides, or amines or ammonium hydroxides. Preference is given to using basic sodium compounds or potassium compounds as the base, for example sodium hydroxide, potassium hydroxide, sodium carbonate or potassium carbonate. It is advantageous to use an aqueous solution of sodium hydroxide or potassium hydroxide, for example having a hydroxide concentration of the solution of from 0.1 to 10 molar, preferably about 1 molar.

The reaction mixture may be worked up after each of the two process steps a) and b). However, the compounds of formula I prepared by the process of the invention may also be synthesized in a one-pot reaction without isolating the thiourea of formula IV formed in step a), and a workup not carried out until after the completion of both process steps. The products are worked up and, if desired, purified by the customary methods, such as extraction, filtration, pH separation, chromatography or crystallization, and the customary dryings.

The starting compounds of formulae II and III are commercially available or can be prepared according to, or in a similar manner to, processes which are described in the literature and familiar to those skilled in the art. The starting compounds may also contain functional groups in protected form or in the form of precursors, and these may then be converted to the desired groups in the compounds of formula I prepared by the process of the invention. Appropriate protecting group techniques are known to those skilled in the art. For example, in compounds of formula III in which X is NR5, the NHR5 group may be protected by an acetyl, trifluoroacetyl or trityl group and be deprotected before carrying out process step b).

X is preferably NR5 or oxygen, more preferably NR5, most preferably NH.

The A radicals, when A is aromatic, and Ar are preferably phenyl or a monocyclic heteroaromatic, more preferably phenyl or a five-membered heteroaromatic, for example thiophene or isoxazole, and all of these radicals may be unsubstituted or substituted. Substituents on the aromatic A and Ar radicals are preferably each independently selected from the group consisting of (C1-C4)alkyl, F, Cl, Br and O(C1-C4)allyl, where some or all of the hydrogen atoms of the alkyl radicals may be replaced by fluorine atoms. Particularly preferred substituents on the Ar and aromatic A radical are, in each case, independently selected from methyl, Cl and Br.

When A is nonaromatic, it is preferably (C1-C4)alkyl, (C2-C5)alkenyl, (C3-$C_5$)cycloalkyl, or (C4-C8)cycloalkenyl, more preferably (C1-C4)alkyl or (C3-$C_5$)cycloalkyl, and some or all of the hydrogen atoms of all radicals may be replaced by fluorine atoms. A substituent on the nonaromatic A radicals is preferably (C1-C4)alkyl.

n, m and o are preferably in each case independently zero or 1, more preferably zero.

R14, R15, R16 and R17 are preferably each independently hydrogen or methyl, more preferably hydrogen, or R14 and R16 together form a bond and R15 and R17 form an aromatic six-membered ring, preferably a benzene ring, or a thiophene ring, and the aromatic six-membered ring and the thiophene ring may be unsubstituted or substituted by 1, 2, 3 or 4 mutually independent R7 radicals, or R14 and R16 are each independently hydrogen or methyl, and R15 and R17 form a saturated 5- or 6-membered ring, preferably a cyclopentane or cyclohexane ring, and the ring may be substituted by a 1, 2, 3, 4, 5 or 6 mutually independent R8 radicals.

In compounds of formulae I, III or IV, it is always the case that either A is aromatic or m is zero and R15 and R17 together with the two carbon atoms to which they are bonded form an aromatic six-membered carbocycle in which one or two carbon atoms may be replaced by nitrogen, or a thiophene ring, or both A and R15 and R17 together with the two carbon atoms to which they are bonded each form aromatic ring systems.

R1, R2, R3 and R4 are preferably each independently hydrogen or methyl, more preferably hydrogen, or R1 and R3 together form a bond and R2 and R4 form an aromatic six-membered ring, preferably a benzene ring, and the aromatic six-membered ring may be unsubstituted or substituted by 1, 2, 3 or 4 mutually independent R7 radicals, or R1 and R3 are each independently hydrogen or methyl and R2 and R4 are a saturated 5- or 6-membered ring, preferably a cyclopentane or cyclohexane ring, and the ring may be substituted by 1, 2, 3, 4, 5 or 6 mutually independent R8 radicals.

R5 is preferably hydrogen or methyl, more preferably hydrogen.

R7 is preferably in each case independently selected from the group consisting of (C1-C4)alkyl, F, Cl, Br, OH and O(C1-C4)alkyl, where some or all of the hydrogen atoms of the alkyl radicals may be replaced by fluorine atoms; the R7 substituents are more preferably each independently Fl, Cl, methyl, methoxy, CF3 or OH.

R8 is preferably in each case independently selected from the group consisting of (C1-C4)alkyl and O(C1-C4)alkyl, where some or all of the hydrogen atoms of the alkyl radicals may be replaced by fluorine atoms.

R10, R11, R12 and R13 are preferably each independently hydrogen, methyl or ethyl, more preferably hydrogen.

The base is preferably an aqueous base, triethylamine or diisopropylethylamine, more preferably an aqueous metal hydroxide solution, in particular a sodium hydroxide or potassium hydroxide solution.

The sulfonyl chloride, $R6SO_2Cl$, is an unsubstituted or substituted benzene- or alkylsulfonyl chloride where R6 is preferably methyl, phenyl, p-tolyl or polymer-bound phenyl.

Polymer-bound sulfonyl chloride is generally an aromatic sulfonyl chloride, for example benzenesulfonyl chloride, which is substituted on the phenyl radical by a polymeric support, for example polystyrene, especially crosslinked polystyrene. For example, sulfonylchloride polystyrene from Novabiochem can be used. In this case, the benzenesulfonic acid is bound to copoly(styrene-1% DVB), 100-200 mesh.

The compounds of formula I may be isolated in the form of their salts. These are obtained by the customary methods, by reacting with acids or bases. Useful acid addition salts include, for example, halides, in particular hydrochlorides or hydrobromides, lactates, sulfates, citrates, tartrates, acetates, phosphates, methylsulfonates, benzenesulfonates, p-toluenesulfonates, adipates, fumarates, gluconates, glutamates, glycerolphosphates, maleates, benzoates, oxalates and pamoates and trifluoroacetates; in the case of the preparation of active ingredients, preferably physiologically acceptable salts. When the compounds contain an acid group, they may form salts with bases, for example alkali metal salts, preferably sodium or potassium salts, or ammonium salts, for example as salts with ammonia or organic amines or amino acids. They may also be present as a zwitterion.

The compounds of formula I may also be present as tautomers or as a mixture of tautomeric structures, for example as the following tautomers:

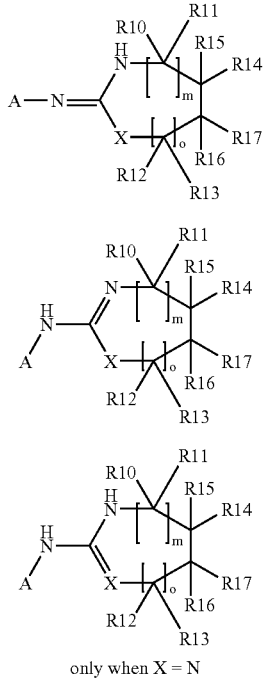

When the compounds of formula I are present in the tautomeric form A, they may be present as double bond isomers or as a mixture of double bond-isomeric structures.

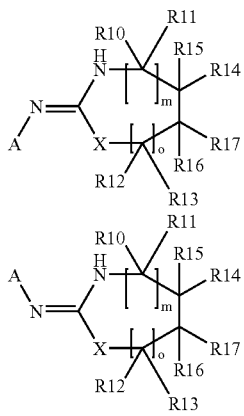

When the compounds of formula I contain one or more centers of asymmetry, these may each independently have either S or R configuration. The compounds may be present as optical isomers, as diastereomers, as cis/trans isomers, as racemates or as mixtures thereof in any ratios.

When m, n or o=0, there is a direct bond between the two adjacent atoms in each case.

Alkyl radicals may be straight-chain or branched. This is also true when they bear substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl) and tert-butyl (=1,1-dimethylethyl). Preferred alkyl radicals are methyl, ethyl and isopropyl. In alkyl radicals, one or more, for example 1, 2, 3, 4, 5, 6, 7, 8 or 9, hydrogen atoms may be substituted by fluorine atoms. Examples of such fluoroalkyl radicals are trifluoromethyl, 2,2,2-trifluoroethyl, pentafluoroethyl, heptafluoroisopropyl. Substituted alkyl radicals may be substituted in any positions, for example by fluorine, by alkyl, for example methyl, ethyl, propyl, butyl, or by cycloalkyl, for example cyclopropyl, cyclobutyl, cyclopentyl or cyclohexyl.

Alkenyl radicals may be straight-chain or branched. This is also true when they bear substituents, for example in fluoroalkenyl radicals. The alkenyl radicals may be unsaturated and also polyunsaturated in different positions. Examples of alkenyl radicals are ethenyl, n-prop-1-enyl, n-prop-2-enyl, isoprop-1-enyl (=1-methylethenyl), n-but-1-enyl, n-but-2-enyl, n-but-3-enyl, n-buta-1,3-dienyl, isobut-1-enyl (=2-methylprop-1-enyl), isobut-2-enyl (=2-methylprop-2-enyl), sec-but-1-enyl (=1-methylprop-1-enyl) and pentenyl. Preferred alkenyl radicals are ethenyl, n-prop-1-enyl, n-prop-2-enyl, n-but-1-enyl, n-but-2-enyl, n-pentenyl, n-pentadienyl, isopentenyl, tert-pentenyl and neopentenyl. In alkenyl radicals, one or more, for example 1, 2, 3, 4, 5, 6, 7, 8 or 9, hydrogen atoms may be substituted by fluorine atoms. Substituted alkenyl radicals may be substituted in any positions, for example by fluorine, by alkyl, for example methyl, ethyl, propyl, butyl, or by cycloalkyl, for example cyclopropyl, cyclobutyl, cyclopentyl or cyclohexyl.

Alkynyl radicals may be straight-chain or branched. This is also true when they bear substituents, for example in fluoroalkynyl radicals. The alkynyl radicals may be unsaturated and also polyunsaturated in different positions. Examples of alkynyl radicals are ethynyl, n-prop-1-ynyl, n-prop-2-ynyl, n-but-1-ynyl, n-but-2-ynyl, n-but-3-ynyl, n-buta-1,3-diynyl, sec-but-2-ynyl (=1-methylprop-2-ynyl), n-pentynyl, n-pentadiynyl, isopentynyl, tert-pentynyl and neopentynyl. Preferred alkynyl radicals are n-prop-1-ynyl, n-prop-2-ynyl, n-but-1-ynyl and n-but-2-ynyl. In alkynyl radicals, one or more, for example 1, 2, 3, 4, 5, 6 or 7, hydrogen atoms may be substituted by fluorine atoms. Substituted alkynyl radicals may be substituted in any positions, for example by fluorine, by alkyl, for example methyl, ethyl, propyl, butyl, or by cycloalkyl, for example cyclopropyl, cyclobutyl, cyclopentyl or cyclohexyl.

Examples of cycloalkyl radicals are cyclopropyl, cyclobutyl, cyclopentyl, cyclohexyl, cycloheptyl or cyclooctyl. Preferred cycloalkyl radicals are cyclopropyl, cyclopentyl and cyclohexyl. In cycloalkyl radicals, one or more, for example 1, 2, 3, 4, 5, 6, 7, 8, 9, 10, 11, 12, 13, 14 or 15, hydrogen atoms may be substituted by fluorine atoms. Substituted cycloalkyl radicals may be substituted in any positions, for example by fluorine, by alkyl, for example methyl, ethyl, propyl, butyl, or by cycloalkyl, for example cyclopropyl, cyclobutyl, cyclopentyl or cyclohexyl.

The cycloalkenyl radicals may be unsaturated in different positions and also polyunsaturated. Examples of cycloalkenyl radicals are cyclobut-1-enyl, cyclobut-2-enyl, cyclopentenyl, cyclopentadienyl, cyclohexenyl, cyclohexadienyl, cycloheptenyl and cyclooctenyl. Preferred cycloalkylene radicals are cyclopentenyl, cyclopentadienyl, cyclohexenyl and cyclohexadienyl. In cycloalkenyl radicals, one or more, for example 1, 2, 3, 4, 5, 6, 7, 8, 9, 10, 11, 12 or 13, hydrogen atoms may be substituted by fluorine atoms. Substituted cycloalkenyl radicals may be substituted in any positions, for example by fluorine, by alkyl, for example methyl, ethyl, propyl, butyl, or by cycloalkyl, for example cyclopropyl, cyclobutyl, cyclopentyl or cyclohexyl.

Aromatic ring systems include phenyl, naphthyl and heteroaryl radicals, and also aromatic six-membered carbocycles in which one or two carbon atoms may be replaced by nitrogen, or thiophene rings.

Phenyl radicals may be unsubstituted or mono- or polysubstituted, for example mono-, di-, tri-, tetra- or pentasubstituted, by identical or different radicals. When a phenyl radical is substituted, it preferably bears one or two identical or different substituents. In monosubstituted phenyl radicals, the substituent may be in the 2-position, the 3-position or the 4-position. Disubstituted phenyl may be substituted in the 2,3-position, 2,4-position, 2,5-position, 2,6-position, 3,4-position or 3,5-position. In trisubstituted phenyl radicals, the substituents may be in the 2,3,4-position, 2,3,5-position, 2,4,5-position, 2,4,6-position, 2,3,6-position or 3,4,5-position. Naphthyl radicals may be joined via all positions, for example via the 1-position or 2-position. Naphthyl radicals may likewise be unsubstituted or mono- or polysubstituted, for example mono-, di-, tri-, tetra- or pentasubstituted, by identical or different radicals. Where a naphthyl radical is substituted, it preferably bears one or two identical or different substituents.

Heteroaryl radicals are aromatic ring compounds in which 1, 2, 3 or 4 ring atoms are oxygen atoms, sulfur atoms or nitrogen atoms, for example 1, 2 or 3 nitrogen atoms, 1 or 2 oxygen atoms, 1 or 2 sulfur atoms or a combination of different hetero atoms. The heteroaryl radicals may be mono- or bicyclic. The heteroaryl radicals may be bonded via all positions, for example via the 1-position, 2-position, 3-position, 4-position, 5-position, 6-position, 7-position or 8-position. Heteroaryl radicals may be unsubstituted or mono- or polysubstituted, for example mono-, di- or trisubstituted, by identical or different radicals.

Useful heteroaryl radicals include, for example:

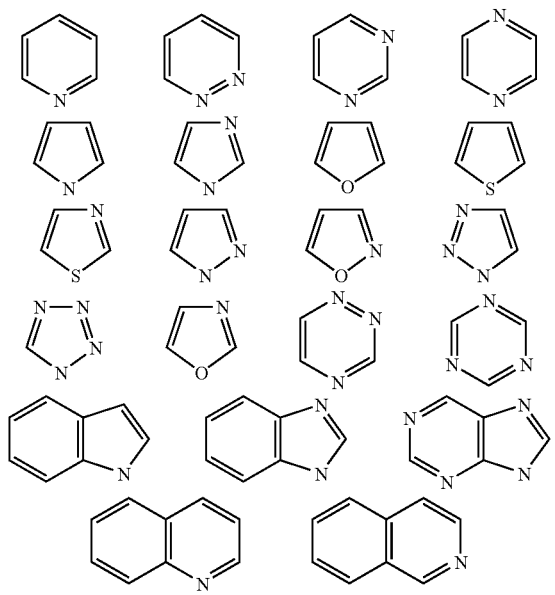

Preferred heteroaryl radicals are monocyclic aromatic ring compounds; particular preference is given to five-membered heteroaryl radicals, for example, thiophene and isoxazole.

If groups or substituents can occur several times in a compound of formula I, Ia, II, IIa, III, IIIa, IV or IVa, they can all independently of one another have the meanings indicated and can in each case be identical or different.

The present invention further provides a process for preparing a compound of formula I

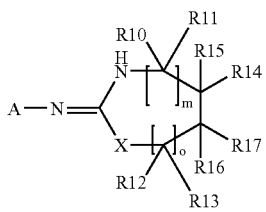

which comprises converting a thiourea of formula IV, using a sulfonyl chloride, R6SO$_2$Cl, in the presence of a base, to a compound of formula I

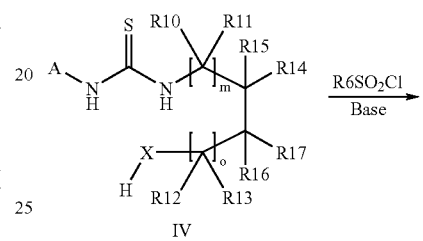

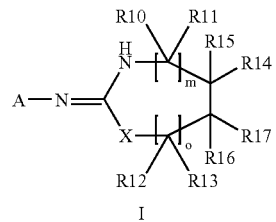

where

A, X, o, m, R6 and R10 to R17 are each as defined above.

All definitions and illustrations for the above-described process apply correspondingly to this process.

In a further embodiment, the present invention provides a process for preparing compounds of formula Ia,

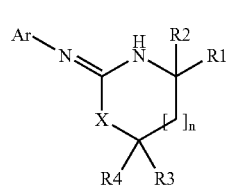

which comprises converting a thiourea of formula Iva, using a sulfonyl chloride, R6SO$_2$Cl, in the presence of a base, to a compound of formula Ia

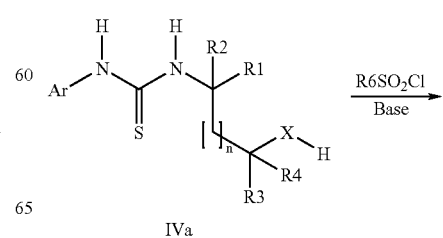

-continued

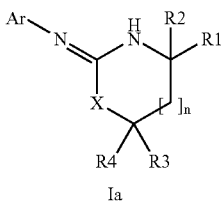

where
Ar, X, n, R1 to R4 and R6 are each as defined above.

All definitions and illustrations of the above-described process apply correspondingly for this process.

The compounds of formula I obtainable by the process according to the invention are valuable intermediates, for example, for the preparation of active pharmaceutical ingredients such as clonidine and its analogs, or are themselves active pharmaceutical ingredients. For example, international patent applications WO 03101984 and WO 03053434 describe compounds which may be prepared by means of the process described herein, and which are suitable as NHE inhibitors, in particular NHE3 inhibitors, for example, for treating respiratory disorders and snoring, and also for improving the respiratory drive, or for treating acute or chronic disorders which are induced by ischemic and/or reperfusion events or by proliferative or by fibrotic events.

EXPERIMENTAL DESCRIPTIONS AND EXAMPLES

Abbreviations abs. absolute
ESI electrospray ionization
rt retention time
THF tetrahydrofuran
TFA trifluoroacetic acid The retention times (rt) reported below relate to LC-MS measurements with the following parameters:
Analytical Methods:

| Method A: | |
|---|---|
| stationary phase: | Merck Purospher 5μ 2 × 55 mm |
| mobile phase: | 95% H₂O (0.05% TFA) → 95% acetonitrile, 3 min; → 95% acetonitrile, 1.5 min; 0.5 ml/min. |

| Method B: | |
|---|---|
| stationary phase: | Merck Purospher 3μ 2 × 55 mm |
| mobile phase: | 95% H₂O (0.08% HCOOH) → 95% acetonitrile (0.1% HCOOH), 5 min; → 95% acetonitrile (0.1% HCOOH), 2 min; → 95% H₂O (0.1% HCOOH), 1 min; 0.45 ml/min. |

| Method C: | |
|---|---|
| stationary phase: | YMC J'sphere H80, 4μ 2.1 × 20 mm |
| mobile phase: | 96% H₂O (0.05% TFA) → 95% acetonitrile, 2 min; → 95% acetonitrile, 0.4 min; 1 ml/min. |

| Method D: | |
|---|---|
| stationary phase | YMC J'sphere H80, 4μ 2.1 × 20 mm |
| mobile phase: | 95% H₂O (0.05% TFA) → 95% acetonitrile, 2.3 min; → 95% acetonitrile, 1 min; 1 ml/min. |

The preparative HPLC was carried out under the following conditions:

| stationary phase: | Merck Purospher RP18 (10 μm) 250 × 25 mm |
|---|---|
| mobile phase: | 90% H₂O (0.05% TFA) → 90% acetonitrile, 40 min; 25 ml/min |

Example 1

Imidazolidin-2-ylidenephenylamine, trifluoroacetic acid salt

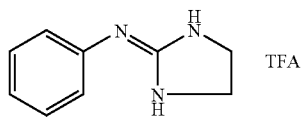

a) 1-(2-Aminoethyl)-3-phenylthiourea

A solution of phenyl isothiocyanate (500 mg) in abs. THF (6 ml) was added dropwise over 20 minutes under argon to a solution of ethylenediamine (5.56 g) in abs. THF (6 ml). Afterwards, the reaction mixture was added to water, acidified with 10% HCl and extracted with ethyl acetate. The aqueous phase was then basified with potassium carbonate and extracted three times with ethyl acetate. The combined organic phases were dried over magnesium sulfate, filtered and concentrated. Subsequently, co-evaporation with toluene was effected twice. 650 mg of the desired product remained.
LC-MS rt (A): 1.96 min
MS (ESI+): 196.2 b) Imidazolidin-2-ylidenephenylamine, trifluoroacetic acid salt 1-(2-Aminoethyl)-3-phenylthiourea (50 mg) was dissolved in THF (1.5 ml) under argon and admixed with a solution of sodium hydroxide (25.6 mg) in water (0.6 ml), and a solution of p-toluenesulfonyl chloride (53.7 mg) in THF was added dropwise within five minutes. After a half hour of stirring, the reaction mixture was added to water, and extraction was effected with ether six times. Subsequently, the combined organic phases were dried over magnesium sulfate, filtered and concentrated. The residue was purified by means of preparative chromatography, and the product-containing fractions were combined, freed of acetonitrile and freeze-dried. After freeze-drying, 20 mg of the desired product were obtained.
LC-MS rt (A): 1.72 min
MS (ESI+): 162.2

Example 2

[1,3]Oxazinan-2-ylidenephenylamine

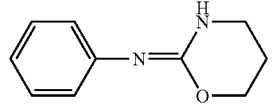

a) 1-(3-Hydroxypropyl)-3-phenylthiourea

A solution of phenyl isothiocyanate (200 mg) in abs. THF (2 ml) was added dropwise under argon and with stirring to a solution of 3-amino-1-propanol (114.5 mg) in abs. THF (2 ml). The reaction mixture was stirred at room temperature for two hours. After removing the solvent, the residue was dissolved in aqueous HCl and washed with ether. Subsequently, the aqueous phase was basified with potassium carbonate and extracted three times with ether. The combined organic phases were dried over magnesium sulfate, filtered and concentrated. The residue was purified by means of preparative chromatography, and the product-containing fractions were combined, freed of acetonitrile, basified and extracted three times with ethyl acetate. The organic phases were combined, dried (MgSO$_4$) and filtered. After removing the solvent, 114 mg of the desired product were obtained.

LC-MS rt (B): 1.99 min
MS (ESI+): 211.20 b) [1,3]Oxazinan-2-ylidenephenylamine

A solution of sodium hydroxide (23.8 mg) and water (0.6 ml) was added under argon and with stirring to a solution of 1-(3-hydroxypropyl)-3-phenylthiourea (50 mg) and THF (1.5 ml). Subsequently, a solution of p-toluenesulfonyl chloride (49.9 mg) and THF (0.5 ml) was added dropwise over fifteen minutes. After stirring for 30 minutes, the reaction mixture was added to water, and extraction was effected three times with ether. The combined organic phases were dried over magnesium sulfate, filtered and concentrated. Chromatography using silica gel (initially 50:1 methylene chloride/methanol, at the end 100:1 methanol/saturated ammonia solution) afforded 27.4 mg of the desired product.

NMR (400 MHz, CDCl$_3$): 7.35-7.18 (4H, m), 6.9-7.0 (1H, m), 4.29 (2H, t), 3.43 (2H, t), 1.96 (2H, q)

Example 3

(2,6-Dichlorophenyl)(octahydrobenzimidazol-2-yliden)amine

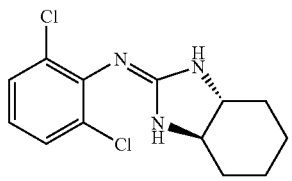 [SMILES: Clc1cccc(Cl)c1N=C1N[C@@H]2CCCC[C@H]2N1]

a) 1-(2-Aminocyclohexyl)-3-(2,6-dichlorophenyl)thiourea

A solution of 1,3-dichloro-2-isothiocyanatobenzene (100 mg) and abs. THF (3 ml) was added dropwise slowly over a half hour to a solution of trans-1,2-diaminocyclohexane (139.9 mg) and abs. THF (3 ml). The solution was stirred at room temperature for a further 90 minutes. The reaction mixture was subsequently added to water, acidified with hydrochloric acid and extracted once with ethyl acetate. Afterwards, the mixture was basified using potassium carbonate, and extracted three times with ethyl acetate. The combined organic phases were dried over magnesium sulfate, filtered and concentrated. 128 mg of the desired product were obtained.

LC-MS rt (B): 1.88 min
MS (ESI+): 318.20 b): (2,6-Dichlorophenyl)(octahydrobenzoimidazol-2-yliden)amine

A solution of sodium hydroxide (15.7 mg) and water (0.6 ml) was added under argon to a solution of 1-(2-aminocyclohexyl)-3-(2,6-dichlorophenyl)thiourea (50 mg) and THF (1.5 ml). Subsequently, a solution of p-toluenesulfonyl chloride (32.9 mg) and THF (0.5 ml) was added dropwise over fifteen minutes. After stirring for 60 minutes, the reaction mixture was added to water and extracted three times with ether. The combined organic phases were dried over magnesium sulfate, filtered and concentrated. 44 mg of the desired product were obtained.

LC-MS rt (B): 1.95 min
MS (ESI+): 284.20

Example 4

(5-Fluoro-1H-benzoimidazol-2-yl)(4-methylthiophen-3-yl)amine hydrochloride

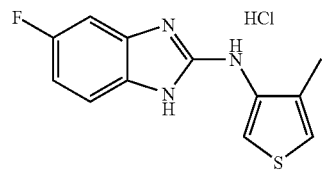 [SMILES: Cc1cscc1Nc1nc2cc(F)ccc2[nH]1 ; Cl]

a) 1-(2-Amino-5-fluorophenyl)-3-(4-methylthiophen-3-yl)thiourea and 1-(2-amino-4-fluorophenyl)-3-(4-methylthiophen-3-yl)thiourea 4-Fluoro-o-phenylenediamine (1.5 g) was dissolved in abs. THF (25 ml) and added dropwise with stirring to 3-isothiocyanato-4-methylthiophene (1.8 g) dissolved in abs. THF (25 ml). On completion of addition, the mixture was stirred at room temperature for 3 h, then a little more 3-isothiocyanato-4-methylthiophene was added and stirring was continued for a further hour. After allowing to stand overnight, the THF was removed, the residue was dissolved in ethanol, carbon was added, and the mixture was heated to boiling and hot-filtered. After cooling, 1.8 g of the desired product were precipitated out of the filtrate with ether.

b) (5-Fluoro-1H-benzoimidazol-2-yl)-(4-methylthiophen-3-yl)amine hydrochloride

The mixture of 1-(2-amino-5-fluorophenyl)-3-(4-methylthiophen-3-yl)thiourea and 1-(2-amino-4-fluorophenyl)-3-(4-methylthiophen-3-yl)thiourea (1.75 g) was dissolved in THF (50 ml) and admixed with a solution of sodium hydroxide (0.622 g) and water (15 ml). Within 5 min, a solution of p-toluenesulfonyl chloride (1.304 g) and THF (10 ml) was added dropwise. On completion of addition, the mixture was stirred at room temperature for a half hour. The reaction mixture was poured onto water, and the aqueous phase was extracted three times. The combined ether phases were dried with magnesium sulfate, filtered and concentrated. The crude product was dissolved in ethyl acetate and adjusted to pH 2 using ethereal HCl. It was precipitated by adding ether. After drying, 750 mg of the desired product were obtained.

LC-MS rt (B): 1.48 min
MS (ESI+): 248.11

Starting from commercially available or known starting materials, the following compounds were prepared in a similar manner to the above examples:

| Example | Amine | Isothio-cyanate | Product | M.p. [° C.] | LC-MS rt [min] | MS (ESI+, M + H+) |
|---|---|---|---|---|---|---|
| 5 | 3,4-diaminothiophene | 2-chloro-3-isothiocyanato-4-methylthiophene | thieno[3,4-d]imidazol-2-yl-(2-chloro-4-methylthien-3-yl)amine x HCl | >300 | | |
| 6 | 3,4-diaminothiophene | 2-(trifluoromethyl)phenyl isothiocyanate | thieno[3,4-d]imidazol-2-yl-(2-trifluoromethylphenyl)amine x HCl | 194-196 | | |
| 7 | 3,4-diaminothiophene | 2,6-dimethylphenyl isothiocyanate | thieno[3,4-d]imidazol-2-yl-(2,6-dimethylphenyl)amine x HCl | >310 | | |
| 8 | 3,4-diaminothiophene | 2,6-difluorophenyl isothiocyanate | thieno[3,4-d]imidazol-2-yl-(2,6-difluorophenyl)amine x HCl | 296 | | |
| 9 | 3,4-diaminothiophene | 2-chloro-6-methylphenyl isothiocyanate | thieno[3,4-d]imidazol-2-yl-(2-chloro-6-methylphenyl)amine x HCl | >310 | | |
| 10 | 3,4-diaminothiophene | 2,4-dichloro-3-isothiocyanatothiophene | thieno[3,4-d]imidazol-2-yl-(2,4-dichlorothien-3-yl)amine x HCl | >300 | | |
| 11 | 1,2-diaminobenzene | 4-chloro-3-isothiocyanatothiophene | benzimidazol-2-yl-(4-chlorothien-3-yl)amine x HCl | 256-260 | | |
| 12 | 4-fluoro-1,2-diaminobenzene | 4-chloro-3-isothiocyanatothiophene | 5-fluorobenzimidazol-2-yl-(4-chlorothien-3-yl)amine | | 0.90 (C) | 268.0 |

-continued

| Example | Amine | Isothio-cyanate | Product | M.p. [° C.] | LC-MS rt [min] | MS (ESI+, M + H+) |
|---|---|---|---|---|---|---|
| 13 | 4,5-difluorobenzene-1,2-diamine | 4-chlorothiophene-3-isothiocyanate | 5,6-difluoro-N-(4-chlorothiophen-3-yl)-1H-benzimidazol-2-amine | | 0.95 (C) | 286.0 |
| 14 | 3-methylbenzene-1,2-diamine | 4-chlorothiophene-3-isothiocyanate | 4-methyl-N-(4-chlorothiophen-3-yl)-1H-benzimidazol-2-amine × HCl | 325-327 | | |
| 15 | cyclohexane-1,2-diamine | 4-chlorothiophene-3-isothiocyanate | N-(4-chlorothiophen-3-yl)-octahydrobenzimidazol-2-amine × HCl | 196-200 | | |
| 16 | cyclohexane-1,2-diamine | 4-chlorothiophene-3-isothiocyanate | N-(4-chlorothiophen-3-yl)-octahydrobenzimidazol-2-amine × HCl | 240-244 | | |
| 17 | cyclohexane-1,2-diamine | 4-chlorothiophene-3-isothiocyanate | trans-N-(4-chlorothiophen-3-yl)-octahydrobenzimidazol-2-amine × HCl | 228-231 | | |
| 18 | 3-chlorobenzene-1,2-diamine | 4-chlorothiophene-3-isothiocyanate | 4-chloro-N-(4-chlorothiophen-3-yl)-1H-benzimidazol-2-amine × HCl | 276-280 | | |
| 19 | 3-fluorobenzene-1,2-diamine | 4-chlorothiophene-3-isothiocyanate | 4-fluoro-N-(4-chlorothiophen-3-yl)-1H-benzimidazol-2-amine × HCl | | 0.89 (C) | 268.0 |

-continued

| Example | Amine | Isothio-cyanate | Product | M.p. [° C.] | LC-MS rt [min] | MS (ESI+, M + H+) |
|---|---|---|---|---|---|---|
| 20 | HO-CH2CH2-NH2 | 3-pyridyl-NCS | pyridin-3-yl-N=oxazolidine | | 0.14 (C) | 164.1 |
| 21 | HO-C(CH3)2-CH2-NH2 | 3-pyridyl-NCS | pyridin-3-yl-N=4,4-dimethyloxazolidine | | 0.20 (C) | 192.1 |
| 22 | HS-CH2CH2-NH2 | phenyl-NCS | phenyl-N=thiazolidine · HCl | | 0.64 (C) | 179.1 |
| 23 | (R)-H2N-CH2-CH(OH)-CH3 | phenyl-NCS | phenyl-N=5-methyloxazolidine | | 0.71 (C) | 177.1 |
| 24 | trans-2-(aminomethyl)cyclohexan-1-ol | 2,6-dichlorophenyl-NCS | (2,6-dichlorophenyl)imino-hexahydrobenzo[1,3]oxazine · HCl | | 1.07 (C) | 299.4 |
| 25 | trans-2-(hydroxymethyl)cyclohexan-1-amine | 2,6-dichlorophenyl-NCS | (2,6-dichlorophenyl)imino-hexahydrobenzo[1,3]oxazine · HCl | | 1.04 (C) | 299.3 |
| 26 | trans-2-aminocyclopentan-1-ol | 2,6-dichlorophenyl-NCS | (2,6-dichlorophenyl)imino-hexahydrocyclopenta[d]oxazole · HCl | | 1.83 (D) | 271.3 |
| 27 | trans-2-aminocyclohexan-1-ol | 2,6-dichlorophenyl-NCS | (2,6-dichlorophenyl)imino-hexahydrobenzo[d]oxazole · HCl | | 1.83 (D) | 285.3 |

-continued

| Example | Amine | Isothiocyanate | Product | M.p. [°C.] | LC-MS rt [min] | MS (ESI+, M + H+) |
|---|---|---|---|---|---|---|
| 28 | 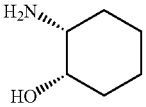 | 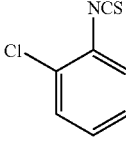 | 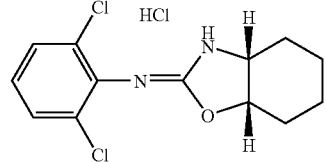 [SMILES: Clc1cccc(Cl)c1N=C1N[C@@H]2CCCC[C@@H]2O1 ; Cl] | | 1.76 (D) | 285.3 |

Example 29

(2,6-Dichlorophenyl)imidazolidin-2-ylidene amine

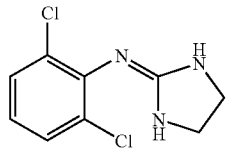 [SMILES: Clc1cccc(Cl)c1N=C1NCCN1]

a) 1-(2-Aminoethyl)-3-(2,6-dichlorophenyl)thiourea

A solution of 2,6-dichlorophenyl isothiocyanate (500 mg) and THF (5 ml) was added dropwise under argon within 20 minutes to a solution of ethylenediamine (3.68 g) and abs. THF (4 ml). After stirring for a further 30 min, the mixture was added to water, acidified with 10% HCl and extracted three times with ethyl acetate. The aqueous phase was made basic using saturated potassium carbonate solution, and extracted three times with ethyl acetate. The combined organic phases were dried over magnesium sulfate, the solvent was removed under reduced pressure and the residue was co-evaporated twice with toluene. After drying in high vacuum, the desired product was obtained as a white solid (532 mg).

LC-MS rt (C): 0.719 min
MS (ESI+): 264.0 b) (2,6-Dichlorophenyl)imidazolidin-2-ylidene amine 1-(2-Aminoethyl)-3-(2,6-dichlorophenyl)thiourea (200 mg) was dissolved under argon in THF (4 ml), admixed with a solution of sodium hydroxide (102 mg) in water (2 ml) and then a slurry of polystyrene-bound toluenesulfonyl chloride (457 mg, 2.9 mmol/g) in THF (4 ml) was added dropwise within five minutes. After stirring at room temperature for 2 h, further polystyrene-bound toluenesulfonyl chloride (65 mg in 2 ml of THF) was added, followed, after a further hour, by further acid chloride (124 mg in 2 ml of THF). After standing overnight, the reaction mixture was filtered, the resin was slurried twice in dichloromethane and the combined phases were concentrated to dryness. The residue was taken up in water/dichloromethane, the phases were separated and the aqueous phase was extracted three times with dichloromethane. The combined organic phases were dried over magnesium sulfate, and the solvent was removed under reduced pressure and the residue subsequently dried under high vacuum. 104 mg of the title compound were obtained.

LC-MS rt (C): 0.65 min
MS (ESI+): 230.1

In a similar manner to Example 29, the following compounds were obtained:

| Example | Amine | Isothiocyanate | Product | LC-MS rt [min] | MS (ESI+, M + H+) |
|---|---|---|---|---|---|
| 30 | 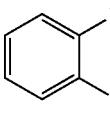 | 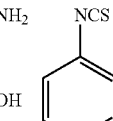 | 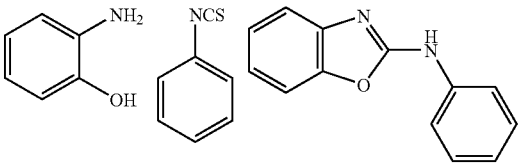 | 1.42 (C) | 211.1 |
| 31 | 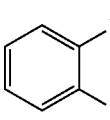 | 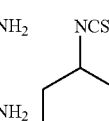 | 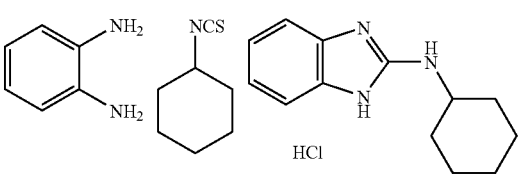 | 0.95 (C) | 216.1 |

What is claimed is:

1. A process for preparing heterocycles of formula Ia,

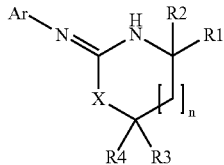

wherein:

X is sulfur, oxygen or NR5, where R5 is hydrogen or (C1-C4)alkyl;

n is zero, 1, 2 or 3;

Ar is phenyl, naphthyl or heteroaryl, each of which may be optionally substituted by 1, 2, 3, 4 or 5 R11 radicals where R11 is in each case independently selected from the group consisting of (C1-C4)alkyl, F, Cl, Br, I, CN, $NO_2$, OH, O(C1-C4)alkyl, and COO(C1-C4)alkyl, and some or all of the hydrogen atoms of the alkyl radicals may be replaced by fluorine atoms;

R1, R2, R3 and R4 are each independently hydrogen, F or (C1-C4)alkyl where some or all of the hydrogen atoms of the alkyl radicals may be replaced by fluorine atoms;

or

R1 and R3 together are a bond, and

R2 and R4, together with the two carbon atoms to which they are attached, form an aromatic six-membered carbocycle in which one or two carbon atoms may be replaced by nitrogen and the aromatic six-membered ring may be substituted by 1, 2, 3 or 4 R7 radicals, where R7 is in each case independently selected from the group consisting of (C1-C4)alkyl, F, Cl, Br, I, CN, $NO_2$, OH, O(C1-C4)alkyl, and COO(C1-C4)alkyl, and some or all of the hydrogen atoms of the alkyl radicals may be replaced by fluorine atoms, where n=0;

or

R1 and R3 are each independently hydrogen or (C1-C4)alkyl and

R2 and R4, together with the two carbon atoms to which they are attached, form a saturated 5-, 6-, 7- or 8-membered carbocycle in which one or two carbon atoms may be replaced by O, S, NH and N(C1-C4)alkyl and which carbocycle may be substituted by 1, 2, 3, 4, 5 or 6 R8 radicals where R8 is in each case independently selected from the group consisting of (C1-C4)alkyl, O(C1-C4)alkyl, and COO(C1-C4)alkyl, and some or all of the hydrogen atoms of the alkyl radicals may be replaced by fluorine atoms, where n=0;

excluding compounds in which Ar is unsubstituted phenyl, X is oxygen or sulfur, R1 and R2 are each independently hydrogen, (C1-C4)alkyl or benzyl, R3 and R4 are each hydrogen and n is zero, and their tautomers and their salts, which process comprises, as shown in scheme 2

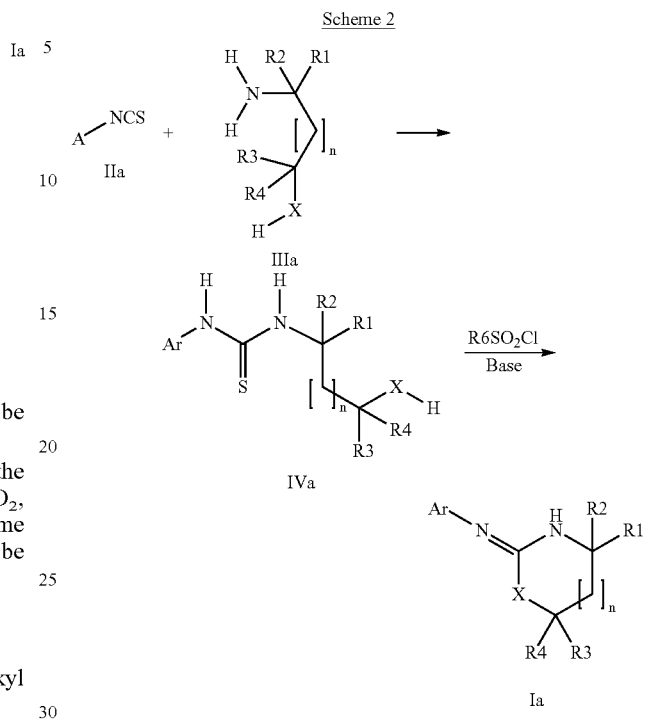

a) reacting an aromatic isothiocyanate of formula IIa with a primary amine of formula IIIa to give a thiourea of formula IVa, and b) converting the thiourea of formula Iva, using a sulfonyl chloride $R6SO_2Cl$ in the presence of a base, to the corresponding compound of formula Ia, where, in the compounds of formulae IIa, IIIa and IVa, Ar, X, n and R1 to R4 are each as defined in formula Ia and R6 is phenyl which is unsubstituted or substituted by methyl, trifluoromethyl, F, Cl or Br.

2. A process for preparing heterocycles of formula Ia,

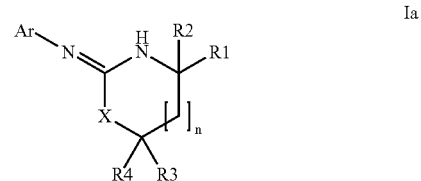

wherein:

X is NR5, where R5 is hydrogen or (C1-C4)alkyl;

n is zero, 1, 2 or 3;

Ar is phenyl, naphthyl or heteroaryl, each of which may be optionally substituted by 1, 2, 3, 4 or 5 R11 radicals where R11 is in each case independently selected from the group consisting of (C1-C4)alkyl, F, Cl, Br, I, CN, $NO_2$, OH, O(C1-C4)alkyl, and COO(C1-C4)alkyl, and some or all of the hydrogen atoms of the alkyl radicals may be replaced by fluorine atoms;

R1, R2, R3 and R4 are each independently hydrogen, F or (C1-C4)alkyl where some or all of the hydrogen atoms of the alkyl radicals may be replaced by fluorine atoms;

or
R1 and R3 together are a bond,
and
R2 and R4, together with the two carbon atoms to which they are attached, form an aromatic six-membered carbocycle in which one or two carbon atoms may be replaced by nitrogen and the aromatic six-membered ring may be substituted by 1, 2, 3 or 4 R7 radicals,
where R7 is in each case independently selected from the group consisting of (C1-C4)alkyl, F, Cl, Br, I, CN, $NO_2$, OH, O(C1-C4)alkyl, and COO(C1-C4)alkyl, and some or all of the hydrogen atoms of the alkyl radicals may be replaced by fluorine atoms,
where n=0;
or
R1 and R3 are each independently hydrogen or (C1-C4)alkyl
and
R2 and R4, together with the two carbon atoms to which they are attached, form a saturated 5-, 6-, 7- or 8-membered carbocycle in which one or two carbon atoms may be replaced by O, S, NH and N(C1-C4)alkyl and which carbocycle may be substituted by 1, 2, 3, 4, 5 or 6 R8 radicals where R8 is in each case independently selected from the group consisting of (C1-C4)alkyl, O(C1-C4)alkyl, and COO(C1-C4)alkyl, and some or all of the hydrogen atoms of the alkyl radicals may be replaced by fluorine atoms,
where n=0;
excluding compounds in which Ar is unsubstituted phenyl, X is oxygen or sulfur, R1 and R2 are each independently hydrogen, (C1-C4)alkyl or benzyl, R3 and R4 are each hydrogen and n is zero,
and their tautomers and their salts,
comprising converting a thiourea of formula Iva, using a sulfonyl chloride, $R6SO_2Cl$, in the presence of a base, to a compound of formula Ia

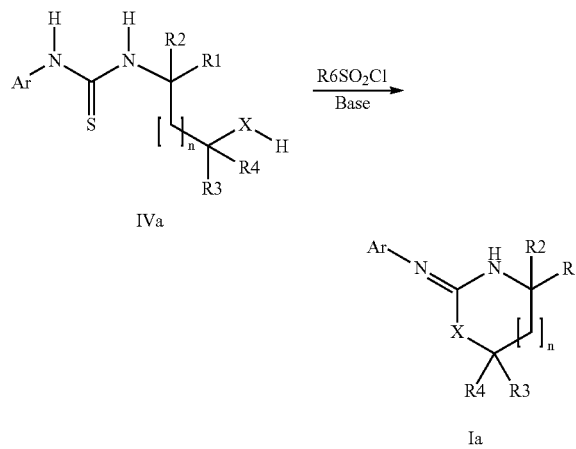

wherein in the compounds of formula Iva,
Ar, X, n, R1 to R4 and R6 are each as defined in formula Ia,
and
R6 is phenyl which is unsubstituted or substituted by methyl trifluoromethyl, F, Cl or Br.

3. The process of claim 1, in which the reaction is carried out as a one-pot reaction.

4. The process of claim 1, wherein steps a) and b) are each independently conducted continuously or batchwise.

5. The process of claim 1, wherein Ar is phenyl, thienyl or isoxazolyl, each of which is optionally substituted by 1, 2, 3, 4 or 5 R11 radicals.

6. The process of claim 1, wherein R6 is phenyl or p-methylphenyl.

7. The process of claim 1, wherein the base used in step b) is sodium hydroxide or potassium hydroxide.

8. The process according to claim 1 wherein Ar is selected from the group consisting of

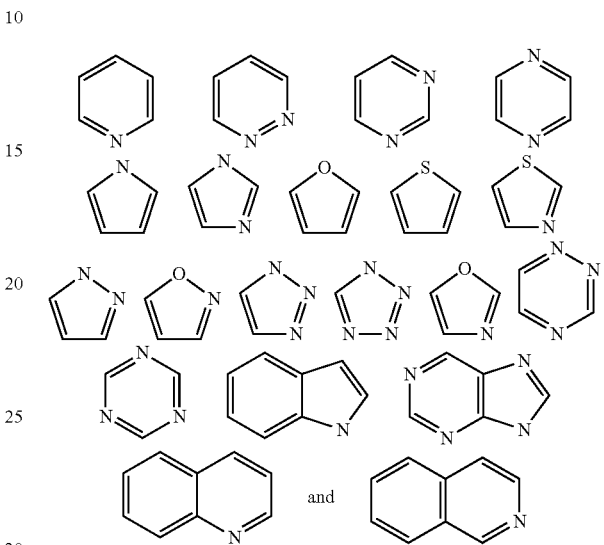

each of which may be optionally substituted by 1, 2, 3, 4 or 5 R11 radicals.

9. The process according to claim 8 wherein Ar is selected from thienyl and isoxazolyl each of which may be optionally substituted by 1, 2, 3 or 4 R11 radicals.

10. The process according to claim 2 wherein Ar is selected from the group consisting of

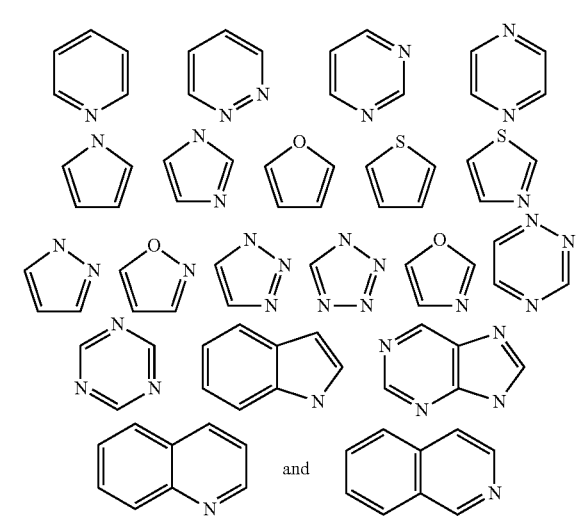

each of which may be optionally substituted by 1, 2, 3, 4 or 5 R11 radicals.

11. The process according to claim 10 wherein Ar is selected from thiophene and isoxazolyl each of which may be optionally substituted by 1, 2, 3, 4 or 5 R11 radicals.

* * * * *